United States Patent [19]
Platz et al.

[11] 4,424,586
[45] Jan. 3, 1984

[54] X-RAY EXAMINATION APPARATUS

[75] Inventors: Winfried Platz, Southington; Steven J. Plummer, Middlefield, both of Conn.

[73] Assignee: Siemens Corporation, Iselin, N.J.

[21] Appl. No.: 312,621

[22] Filed: Oct. 19, 1981

[51] Int. Cl.$^3$ .............................................. A61B 6/12
[52] U.S. Cl. ................................. 378/197; 378/204; 378/181
[58] Field of Search ............... 378/167, 193, 210, 197, 378/62, 204, 190

[56] References Cited

U.S. PATENT DOCUMENTS
2,582,776  1/1952  Greenberg et al. ................. 378/197

FOREIGN PATENT DOCUMENTS
2141461  of 0000  Fed. Rep. of Germany .
542798   1/1942   United Kingdom ................ 378/197

OTHER PUBLICATIONS
Siemens AG, West Germany, Brochure "Ceiling Support 3D/3D-M for Attachment of X-ray Tube Assemblies and Image Intensifiers".
Siemens AG, West Germany, Brochure "Arcoskop 100-3D, Data".

Primary Examiner—Alfred E. Smith
Assistant Examiner—T. N. Grigsby
Attorney, Agent, or Firm—Karl F. Milde, Jr.

[57] ABSTRACT

The X-ray apparatus contains an X-ray tube and a transition device for moving the X-ray tube between a vertical and a horizontal emission position. A first film cassette tray may be provided for vertical exposures. A second film cassette tray is provided for horizontal exposures. The X-ray apparatus further contains a mechanism for operationally connecting the second tray to the X-ray tube. This mechanism is designed such that the second tray is positioned in a waiting position outside the vertical X-ray beam when the X-ray tube is in its vertical emission position and such that the second tray is automatically transferred from the waiting position to a horizontal exposure position when the X-ray tube is moved from its vertical emission position to its horizontal emission position. The mechanism preferably contains a large number of arms and levers.

23 Claims, 6 Drawing Figures

X-RAY EXAMINATION APPARATUS

BACKGROUND OF THE INVENTION

1. Field of the Invention

This invention generally relates to X-ray apparatus having an X-ray tube and a film cassette tray for taking exposures in X-ray diagnosis. More particularly, this invention relates to an X-ray apparatus which is equipped for taking exposures in a vertical and horizontal direction.

2. Description of the Prior Art

In the brochure "Ceiling Support 3D/3 D-M For Attachment of X-ray Tube Assemblies and Image Intensifiers", published by Siemens Aktiengesellschaft, West Germany, is disclosed a ceiling support device which is designed as a carrier for an X-ray tube assembly and an image intensifier. This support device especially allows utilization of the X-ray tube assembly and the image intensifier in X-ray diagnosis. The ceiling support device is independent of any floor support. One of the main parts of the support device is a telescopic column or crane extending in a vertical direction from the ceiling. The telescopic column may be movable in longitudinal and transverse ceiling tracks. It may also be fixed to the ceiling so that only vertical movements are possible. For instance, the ceiling support device may be applied in connection with a bucky table. In one version of the known ceiling support (see FIG. 3 of the brochure "Ceiling Support 3D/3D-M", supra) a horizontally extending mounting arm is attached to the lower end of the column. The X-ray tube assembly which comprises an X-ray tube and a collimator is attached to one end of this mounting arm. Attached to the other end of the mounting arm is a control box. This box contains control switches, an angle indicator allowing oblique angles to be easily set and reproduced, a light beam indicator permitting exact alignment of a control beam with the center of a cassette tray located in the bucky table, and a tape measure showing the focus/film distance for radiographs using horizontal or oblique beam projections. Radiographs with vertical beam projection are also possible. The switches in the control box are lock releases for horizontal and vertical movements, a latch release for rotational movements, and a lock release for oblique settings.

The known ceiling support allows for X-ray expposures of a patient in a vertical and a horizontal direction. As already mentioned, a first film cassette tray is positioned in the table top beneath the patient. In another version the X-ray tube is located beneath the patient and the film cassette above the patient. This also allows for horizontal exposures, when the second film tray is used which is located in the bucky wall stand. It will be noted that the two trays are not operationally connected to each other.

In order to move the X-ray tube from a position where radiation is emitted in a vertical direction to a position where radiation is emitted in a horizontal direction, the X-ray tube assembly must be rotated about the longitudinal axis of the mounting arm. A cassette tray for horizontal exposures is provided in the separate bucky wall stand (see FIG. 4 of the brochure "Ceiling Support 3D/3M" supra). Such a tray is not provided on the column or on the mounting arm. In other words: the known ceiling support takes exposures in a vertical direction of radiation using the film cassette tray which is built into the bucky table. For horizontal exposures, the additional wall stand having built-in a second film cassette is required. Therefore, an apparatus equipped for horizontal and vertical exposures becomes expensive. In addition, switching from the vertical to horizontal radiation and exposure position is time consuming, since adjustment work is needed to position the second cassette in a vertical position in front of the X-ray tube assembly. Whenever this position is taken, the focus-film-distance has to be measured to determine the correct exposure time. Since the second film tray is arranged in a wall-stand, access to the patient is limited especially when lateral exposures are to be taken.

In German Offenlegungsschrift or published application 21 41 461 is disclosed an X-ray apparatus containing a ceiling support device or column, an X-ray tube and a film cassette. To the lower end of the column is connected a transverse arm which pivots about an axis that is arranged perpendicularly to the longitudinal axis of the column. To one end of this transverse arm is pivotly connected a first support arm, to the free end of which is pivotally attached the X-ray tube. To the other end of the transverse arm is pivotally connected a second support arm to the free end of which is pivotally connected the film cassette. The pivoting axes of the first and second arms are parallel to the pivoting axis of the transverse arm. There is provided a driving mechanism by which, independently from the rotational position of the transverse arm, the orientation of the first support arm is maintained and by which the central beam of the X-ray beam is permanently kept parallel to the longitudinal axis of the arm. This X-ray apparatus is useful for many applications. However, due to its sophisticated driving mechanism, its production is too expensive for applications where X-ray exposures only in a horizontal and a vertical direction have to be taken. In addition, free access to the patient is limited, and problems may arise when an X-ray film tray is to be used instead of the X-ray image intensifier.

Frequently examinations are made of a patient's internal organs as for instance the stomach. In these examinations it is of interest to the physician to observe for example the action of a barium slurry from the stomach walls of a patient resting on a stretcher or medical examination table. In these examinations, X-rays are taken laterally, that is transversely to the longitudinal axis of the resting patient. When the patient lies on his or her side, such exposures are taken in the direction from the front to the back, or vice versa, and when the patient lies on his or her back or stomach, such exposures are taken in the direction from the left side to the right side, or vice versa. This means that the cone of X-ray leaves the X-ray tube approximately horizontally and is received by an X-ray film which is positioned approximately vertically. It is desirable to have an X-ray apparatus which can be used for these examinations, using horizontal irradiation, but which can easily be changed over such that conventional examinations using vertical irradiation can be performed.

SUMMARY OF THE INVENTION

Objects

It is an object of this invention to provide an X-ray apparatus, wherein an X-ray tube is used for vertical exposures as well as for horizontal exposures, wherein a first film cassette tray may be used for vertical exposures and a second film cassette tray is used for horizontal exposures, wherein a quick transition from a vertical exposure position to a horizontal exposure position, and vice versa, can easily be performed, and wherein access to a patient under X-ray examination is not impeded by the unused film cassette tray when exposures are to be taken.

It is still another object of this invention to provide an X-ray apparatus wherein the means for performing a transition from a vertical exposure position to a horizontal exposure position, and vice versa, are of simple design.

It is still another object of this invention to provide an X-ray apparatus wherein a transition from a vertical to a horizontal exposure position, and vice versa, does not require must strength on the part of the operator.

Summary

According to this invention, an X-ray apparatus contains an X-ray tube and a transition device for moving the X-ray tube between a first and a second position. In the first position, the X-ray tube emits a beam of X-rays substantially in a vertical direction, and in the second position the X-ray tube emits a beam of X-rays substantially in a horizontal direction. A first film cassette tray may be provided for vertical exposures. The plane of this film cassette is positioned substantially horizontally such as to receive the vertical beam of X-rays from the X-ray tube when the X-ray tube is in its first position. This first cassette may be contained in an examination table. The X-ray apparatus contains a second film cassette tray. This tray has a plane which is an exposure position is positioned substantially vertically such as to receive the horizontal beam of X-rays from the X-ray tube when the X-ray tube is in its second position.

The X-ray apparatus further contains a device or mechanism for operationally connecting or attaching the second film cassette tray to the X-ray tube. By this connecting device the second film cassette tray is positioned in a waiting position outside the vertical beam of X-rays when the X-ray tube is in its first position. This connection device is also designed for transferring the second film cassette tray from the waiting position to the exposure position when the X-ray tube is moved from its first position to its second position.

In other words: the second X-ray film cassette tray is automatically brought into the correct horizontal exposure position when the X-ray tube is moved from its first position into its second position. When the X-ray tube is in a vertical exposure position and is directed towards the first film cassette, the second film cassette tray is kept in the waiting position outside the beam of X-rays. Therefore, the second tray does not interfere with vertical exposures. In addition, it does not impede access to a patient subject to X-ray examination.

In particular, the X-ray tube, the second cassette tray and the transition device may be operationally connected to a column which is suspended from a ceiling.

Preferably, the transition device and/or the connection device may contain an arrangement of levers.

The foregoing and other objects, features and advantages of the invention will be apparent from the following more particular description of the preferred embodiments of the invention, as illustrated in the accompanying drawings.

DESCRIPTION OF THE PREFERRED EMBODIMENTS

Figure 1:
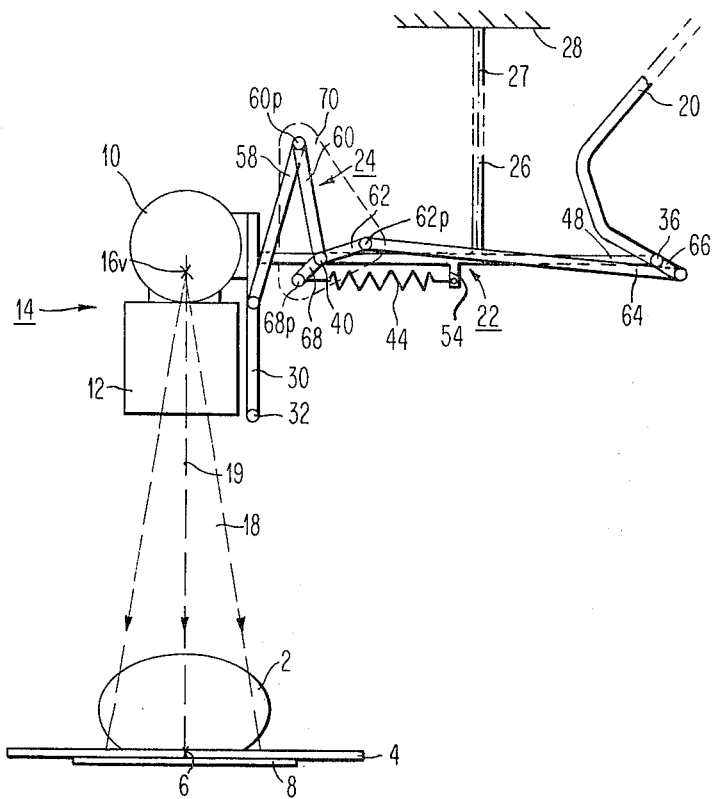
FIG. 1 is a schematic side view of a first embodiment of the invention, wherein the X-ray tube is in a vertical emission position, and wherein the second film cassette tray is in a non-use position.
Figure 2:
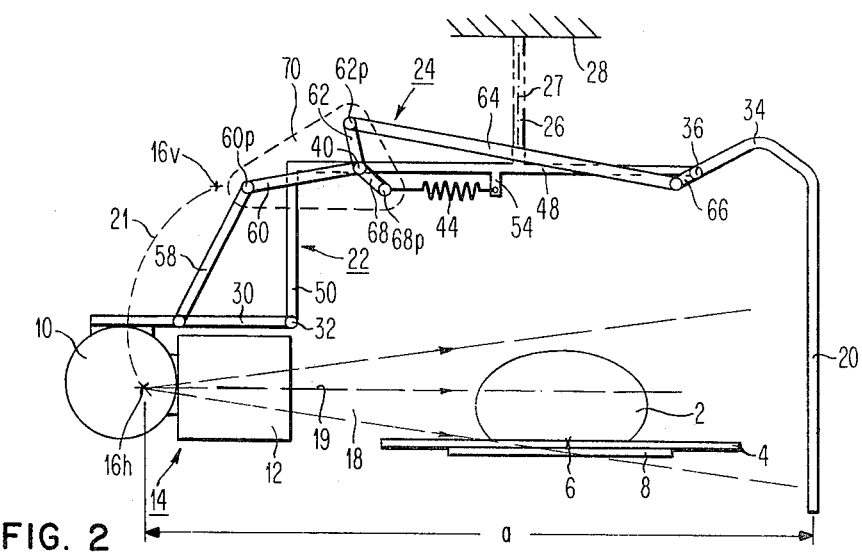
FIG. 2 is a schematic side view of the first embodiment according to FIG. 1, wherein the X-ray tube is in its horizontal emission position, and wherein the second film cassette tray is in its exposure position.

With reference to FIGS. 1 and 2 an X-ray apparatus is illustrated which can be used for taking vertical exposures as well as for horizontal exposures from a patient 2. The patient 2 lies on a table top 4 which is part of a conventional patient examination table. The table top 4 can be moved horizontally along its longitudinal axis 6 in a direction perpendicular to the plane of the drawing. The table top 4 or the whole table can also be moved in a horizontal direction perpendicular to the longitudinal axis 6.

To the lower side of the table top 4 is attached a first film cassette tray 8 for housing a film cassette therein.

One of the principal parts of the X-ray apparatus is an X-ray tube 10 which is combined with a collimator 12 to form a tube assembly 14. The focus of the X-ray tube 10 is denoted as 16. The X-ray tube 10 is used for vertical exposures as well as for horizontal exposures. Thus, according to FIG. 1, the X-ray tube 10 can assume a first position in which it emits a diverging beam 18 of X-rays substantially in a vertical direction downwardly toward the patient 2 and the first film cassette tray 8. According to FIG. 2 the X-ray tube 10 can assume a second position in which it emits a diverging beam 18 of X-rays substantially in a horizontal direction towards the patient 2. The central beam of the beam 18 is denoted by 19.

The first film cassette tray 8 is used for vertical exposures as can be seen in FIG. 1. This first film cassette tray 8 has a plane which in its exposure position is positioned substantially horizontally such as to receive the vertical beam 18 of X-rays from the X-ray tube 10 when the X-ray tube 10 is in its first position. There is also provided a second film cassette tray 20 which is used for horizontal exposures, as can be seen in FIG. 2. The second film cassette tray 20 has a plane which in its exposure position is positioned substantially vertically such as to receive the horizontal beam 18 of X-rays from the X-ray tube 10 when the X-ray tube 10 is in its second position. In FIG. 1, the second film cassette tray 20 is positioned in a waiting position outside the vertical beam 18 of X-rays, and in FIG. 2 the second film cassette tray 20 is positioned in an exposure position, thereby receiving X-rays penetrating the body of the patient 2.

As will be described in more detail below, there is provided a first mechanism or transition device for moving the X-ray tube 10 from its first to its second position, and vice versa. There is also provided a second mechanism or transition device for transferring the second film cassette tray 20 from the waiting position to the exposure position, and vice versa, when the X-ray tube 10 is moved from its first position to its second position, and vice versa. In other words, a movement of the second film cassette tray 20 is coupled to a movement of the X-ray tube 10, and vice versa. Thus, the second film cassette tray is automatically transferred from its waiting position into its horizontal exposure position when the X-ray tube 10 is moved from its vertical first position to its horizontal second emission position. Due to the fact that the waiting position of the second film tray 20 is chosen to be outside the path of X-rays and above the exposure position, the second film cassette tray 20 does not impede the access to the patient.

In FIG. 2, the position of the focus 16 during a vertical exposure is denoted by 16v, while its position during a horizontal exposure is denoted by 16h. Movement from one position to the other is along a quarter circle 21.

The transition devices for moving the X-ray tube 10 from its first to its second position and for simultaneously moving the second film cassette tray 20 from its waiting position into its exposure position and vice versa, comprises a rigid arm assembly or mounting device 22 and a lever assembly 24 which is movable with respect to the mounting device 22. The mounting device 22 is attached to the lower end of a support column 26. The support column 26 is suspended from a ceiling 28 in a vertical direction. Preferably the column 26 is a telescopic column of conventional design. With respect to the longitudinal axis 27 of the support column 26, the mounting device 22 has a first or left side and a second or right side. The X-ray tube 10 is pivotly connected to the left side while the second film cassette tray 20 is pivotally connected to the right side.

The X-ray tube 10 is attached to a first support arm or lever 30 and tiltable about a first horizontal axis 32. The second film cassette tray 20 is connected to a curved second support arm or lever 34 and tiltable about a second horizontal axis 36. Both axes 32 and 36 are parallel to each other. The first axis 32 is vertically lower than the second axis 36. Both axes 32 and 36 are provided at the left and right end portion, respectively, of the mounting device 22. As can be seen from FIGS. 1 and 2, the X-ray tube 10 is rotated about the first horizontal axis 32 between its first and second position, and the second film cassette tray 20 is rotated about the second horizontal axis 36 between its waiting position and its exposure position.

Coordination of both movements is performed by means of the lever or arm assembly 24. This assembly 24 is rotatable about a third horizontal pivoting axis or common pivotal axis 40 with respect to the mounting device 22. This third horizontal pivoting axis 40 is parallel to the axes 32 and 36. It is approximately on the same height as the second axis 36.

Since the second film cassette tray 20 is operatively connected to the X-ray tube 10, operation of the arm assembly 24 is by hand. That is, the operator (physician, nurse) rotates the X-ray tube 10 about the first horizontal axis 32, and a rotation of the second film cassette tray 20 about the second horizontal axis 36 will automatically follow. This operation can be facilitated by use of a spring 44 which balances the weight of the X-ray tube assembly 14 on the one hand and the second film cassette tray 20 on the other hand. Thus, when the operator rotates the second film cassette tray 20 about the second horizontal axis 36, a corresponding rotation of the X-ray tube 10 will automatically result.

The three horizontal axis 32, 36 and 40 are located below the lower end of the support column 26. The axes 32, 36 and 40 are fixed with respect to the mounting device 22.

The mounting device 22 basically contains an elongated horizontal carrier piece 48, an extension piece 50 extending downwardly from the left end thereof, and a small connecting arm 54 connected to the middle portion of the carrier piece 48. The first horizontal axis 32 is located at the lower end of the vertical extension piece 50, the second horizontal axis 36 is located at the right end of the carrier piece 48, and the third horizontal axis 40 is located between the left end of the carrier piece 48 and the attachment of the supporting column 26. These design features make sure that in the horizontal exposure position (see FIG. 2) the X-ray tube 10 and the second film cassette tray 20 are located below the lower end of the support column 26.

The arm assembly 24 is a positioning and transferring or moving device. The moving device for the X-ray tube 10 contains a first knee joint which comprises two pivotally connected arms 58 and 60. The outer end of the arm 58 is connected to the middle portion of the first support arm 30, and the outer end of the arm 60 is pivotally connected to the third horizontal axis 40. The moving device for the tray 20 contains a second knee joint which comprises two arms 62 and 64 which are pivotally connected to each other. The outer end of the arm 62 is pivotly connected to the third horizontal axis 40, and the outer end of the arm 64 is pivotally connected to an arm 66 which is an extension of the curved arm 34 reaching beyond the second horizontal pivotal axis 36. Another arm 68 is also pivotally connected to the third horizontal axis 40. The other end of this arm 68 is connected to the spring 44. The spring 44 is a compression spring, preferably a gas compression spring. The arms 60, 62 and 68 form a star. They are jointly rotatable about the third horizontal axis 40.

As indicated in FIGS. 1 and 2, the arms 60, 62 and 68 may be combined in a plate 70. Such a plate 70 has three rotation axes 60p, 62p and 68p, respectively, representing the pivoting axis of the first and second knee joint and the connecting point of the spring 44, respectively. Again, a common pivotal axis or third horizontal axis 40 is provided in the mounting device 22 for pivoting the plate 70 thereabout. The three connection points or pivoting axes 60p, 62p and 68p may be realized by small pins.

It should be mentioned that the arms 58 and/or 64 may include insert pieces for adjustments of the position of the X-ray tube 10 and of the second film cassette tray 20, respectively.

By means of the device 22 and of the assembly 24, a quick transition from a vertical exposure position (see FIG. 1) to a horizontal exposure position (see FIG. 2), and vice versa, can easily be performed. The spring 44 facilitates such a transition. This transition, therefore, does not require much strength on the part of the operaton (physician, nurse).

Due to the mechanical parts used which can be manufactured with only little play, a predetermined distance a between the focus 16 of the X-ray tube 10 and a film enclosed in the second film cassette tray 20 is achieved in the horizontal exposure position, even after a large number of transitions between the first and the second position. The distance a between the focus 16 and the second tray 20 may be, for instance, one meter. Due to the simplicity of the design, the X-ray apparatus can be operated very easily by the personnel (physician, X-ray assistant). This is especially true as far as adjustments with respect to the patient 2 are concerned. The X-ray apparatus including the transition mechanisms has a compact design which is of advantage for the personnel working on the patient 2.

Figure 3:
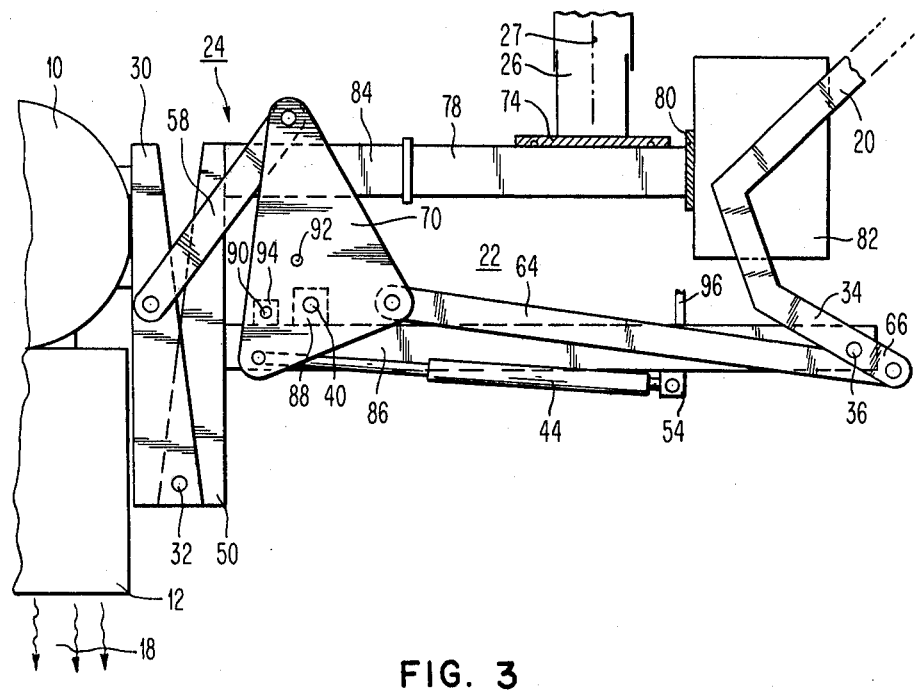
FIG. 3 is a schematic side view of a second embodiment of an X-ray apparatus according to the invention, wherein the X-ray tube is in its vertical X-ray emission position.
Figure 4:
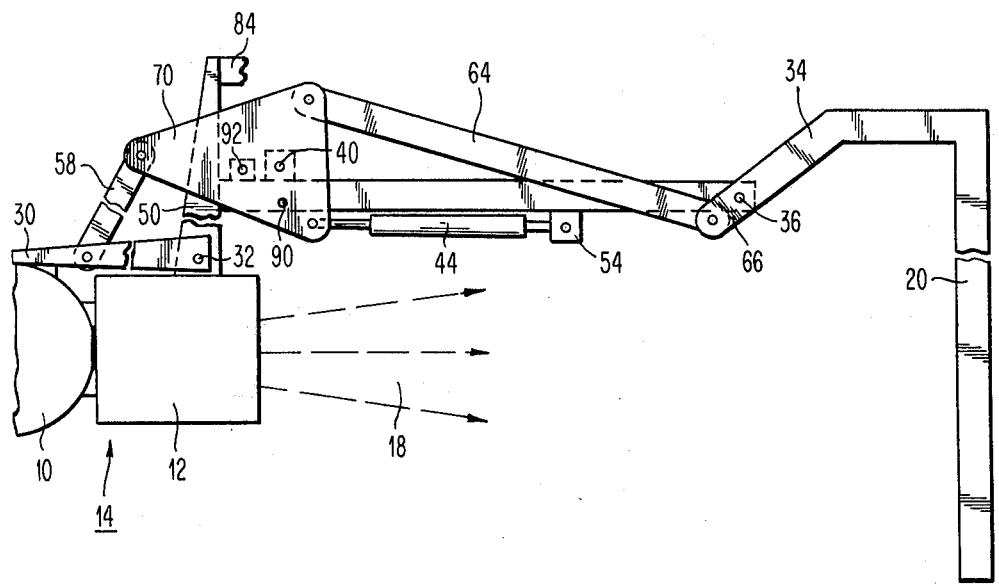
FIG. 4 is a schematic side view of the embodiment of FIG. 3, wherein the X-ray tube is in its horizontal X-ray emission position.
Figure 5:
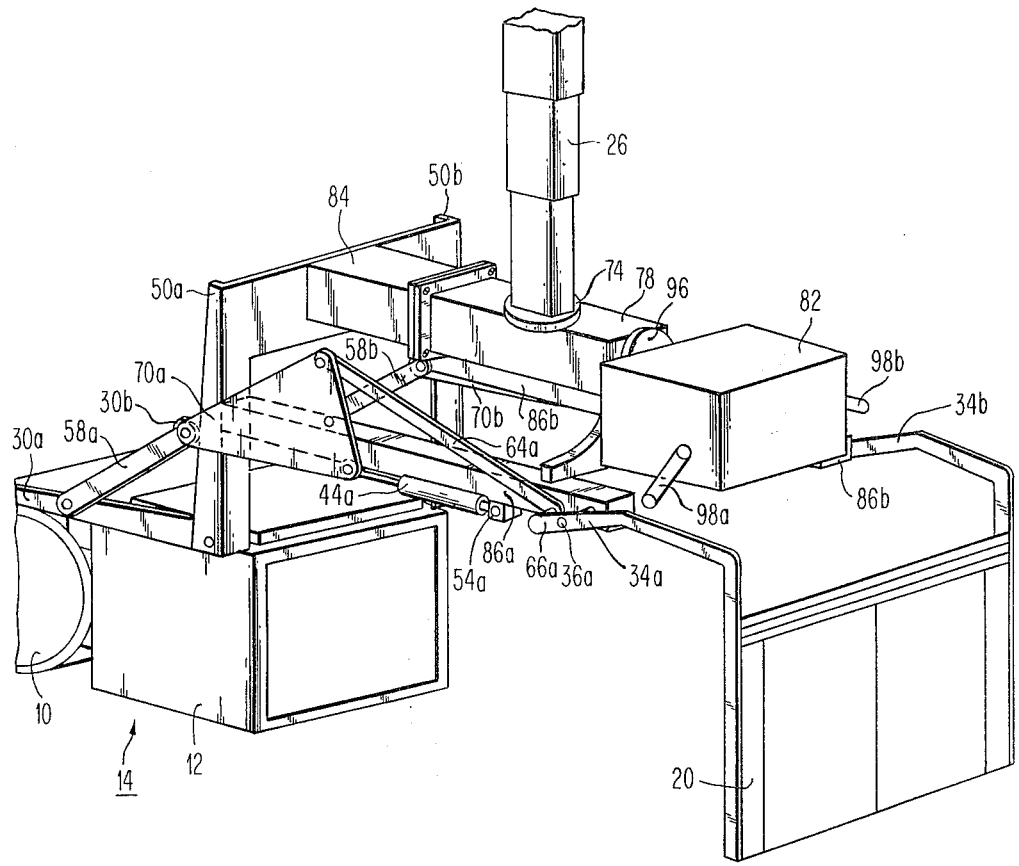
FIG. 5 is a perspective representation of the second embodiment of the apparatus illustrated schematically in FIG. 4.

In FIGS. 3 through 5 an X-ray apparatus having a support column 26, an X-ray tube assembly 14, a second film cassette tray 20 and a specific lateral attachment device attaching the X-ray tube assembly 14 and the second film cassette tray 20 to the collumn 20 is illustrated. This embodiment illustrates that conventional ceiling transports (see brochure "Ceiling Support", supra) which are already in use may be equipped with a lateral attachment, thereby making possible vertical and horizontal exposures.

In FIGS. 3 and 4 a side view of the preferred embodiment of an X-ray apparatus according to the invention is illustrated. Elements having the same function as corresponding elements in FIGS. 1 and 2 are referred to by the same reference numerals.

In this embodiment a turntable or rotation device 74 is attached to the lower end of the telescopic support column 26. The device 74 is provided for rotating all elements attached thereto about the longitudinal axis 27 of the column 26. Thus, the whole X-ray assembly can be rotated about the vertical axis 27 in order to obtain a good adjustment with respect to the patient's body.

Firmly attached to the lower side of the rotating device 74 is a mounting arm 78. This mounting arm 78 constitutes a part of the mounting device 22. The mounting arm 78 extends in a horizontal direction. To its right end is attached a rotating device 80. The rotating device 80 supports an operating control box 82 which houses conventional control elements necessary for the operation of the X-ray apparatus. Thus the control box 82 may be rotated about a horizontal axis. The box 82 may be provided with handles 98a and 98b (shown in FIG. 5) for performing such rotational movements. To the left end of the mounting arm 78 is firmly connected a connection piece 84 which is also a part of the mounting device 22. The vertical extension piece 50 is firmly connected to the left end of the connection piece 84. This vertical extension piece 50 in turn supports a horizontal support arm 86 which extends parallel to the arm combination 78, 84. The horizontal support arm 86 contains the second and third horizontal axis 36 and 40, respectively. The three horizontal axes 32, 36 and 40 are arranged perpendicularly to the longitudinal axis of the horizontal mounting arm 78 and thus also perpendicularly to the horizontal support arm 86. The first horizontal axis 32 is again provided in the lower portion of the vertical extension piece 50. The third horizontal axis 40 is contained in a block 88 mounted on the arm 86.

Figure 6:
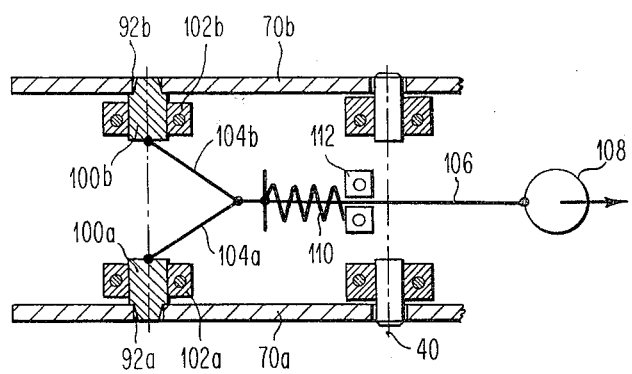
FIG. 6 is a schematic top view of locking devices used in the X-ray apparatus illustrated in FIGS. 3 through 5.

According to FIGS. 3 and 4, safety precautions are taken in order to prevent non-intended movements of the X-ray assembly 14 and the second cassette tray 20. These safety precautions include a locking device which comprises a first and a second aperture 90 and 92, respectively, provided in the plate 70. In the vertical X-ray emission position (see FIG. 3) the aperture 90 is aligned with a pin slidably mounted in a block 94. The block 94 is fastened on the support arm 86. The pin extends through the aperture 90, thereby preventing the plate 70 from rotating about the third horizontal axis 40. In the horizontal X-ray emission position (see FIG. 4), the aperture 92 is aligned with the pin. The pin now extends through the aperture 94, thereby again preventing the plate 70 from rotating about the third horizontal axis 40. More details of a locking device which locks the X-ray tube 10 in its first and second position are illustrated in FIG. 6.

In the embodiment according to FIGS. 3 and 4, the X-ray tube 10 again is arranged on the left side, and the second film cassette tray 20 again is arranged on the right side of the longitudinal axis 27 of the column 26. Again, a compression spring 44 is provided for balancing the weights of the moving parts, thereby facilitating the hand operation of the transition mechanism.

One important feature of the embodiment illustrated in FIGS. 3 and 4 resides in the fact that the connection arm 84 and the elements directly or operationally connected therewith can easily be attached to the mounting arm 78. In a prior art design, an X-ray tube assembly is directly connected to the mounting arm 78. Due to the present construction, such prior art design can easily be modified by removing the X-ray tube assembly 14 from the mounting arm 78, attaching it to the first support arm 30, and by attaching a completed unit comprising the arms 50, 85, 86, the devices 22 and 24, the X-ray tube assembly 14 and the tray 20 to the left side of the mounting arm 78.

In FIG. 5 is illustrated a perspective view of the X-ray apparatus shown in FIGS. 3 and 4. Like elements are referred to by like reference numerals. Those elements which are located on the front side of the X-ray apparatus are designated with a suffix "a", and those parts which are located at the back side are denoted with a suffix "b".

From FIG. 5 it will be obvious that two parallel mechanisms are used for achieving coordinated transitions of the X-ray tube assembly 40 and the second X-ray film tray 20. The X-ray tube assembly 14 is supported by the parallel arms 30a and 30b, while the second film cassette tray 20 is supported by the parallel arms 34a and 34b. The arm 30a is operatively connected to the arm 34a through a lever mechanism, as illustrated in FIGS. 3 and 4. Similarly, the arm 30b is operatively connected to the arm 34b through a lever mechanism designed in a mirror-inverted fashion with respect to the lever mechanism illustrated in FIGS. 3 and 4. A plate 96 fastened to the two parallel support arms 86a and 86b support the box 82 which is rotatably attached to the arm 78.

In FIG. 6 a blocking device for blocking the X-ray tube 12 and the second tray 20 in their predetermined rotational positions is illustrated. The blocking device works together with the two parallel triangular plates 70a and 70b of the lever mechanisms (see FIG. 5). In accordance with FIGS. 3 and 4, these plates 70a and 70b are provided with apertures 92a and 92b. Pins 100a and 100b are provided to slide in sleeve bearings 102a and 102b and to extend into the aperatures 92a and 92b, respectively. These pins 100a and 100b can be retracted by levers 104a and 104b, respectively. These levers 104a, 104b can be pulled back by means of an actuation rod 106 and a ring 108. Instead of a ring 108, a handle may be used. In order to insert the outer ends of the pins 100a and 100b firmly into the apertures 92a and 92b, respectively, a spring 110 is provided on the actuation rod 106. The spring 110 is biased against a block 112 which is in some way connected to the triangular plates 70a and 70b. By pulling the ring 108 in the direction of the arrow 112, the pins 100a and 100b are retracted from the holes 92a and 92b, thereby releasing the plates 70a and 70b, respectively, for rotation.

While the forms of the X-ray apparatus herein described constitute preferred embodiments of the invention, it is to be understood that the invention is not limited to these precise forms of assembly, and that a variety of changes may be made therein without departing from the scope of the invention.

What is claimed is:

1. In an X-ray apparatus containing:
 an X-ray tube;
 means for moving said X-ray tube between
  a first position in which said X-ray tube is adapted to emit a beam of X-rays in a first direction, and
  a second position in which said X-ray tube is adapted to emit a beam of X-rays in a second direction substantially normal to said first direction;
 a film cassette tray having a plane in an exposure position to receive said beam of X-rays from said X-ray tube when said X-ray tube is in its second position; and
 means operationally connected to said X-ray tube for positioning said film cassette tray in a waiting position outside said beam of X-rays when said X-ray tube is in its first position and for transferring said film cassette tray from said waiting position to said exposure position when said X-ray tube is moved from its first position to its second position.

2. The improvement according to claim 1, further comprising:
 a support column for suspending from a ceiling in a vertical direction, said column having an upper and a lower end;
 a mounting device connected to said lower end of said column, said mounting device having a first and a second side, said sides being opposite to each other with respect to the longitudinal axis of said support column,
 first pivoting means for pivotly attaching said X-ray tube to said mounting device, said X-ray tube thereby being tiltable about a first horizontal axis between said first and second position; and
 second pivoting means for pivotly attaching said film cassette tray to said mounting device, said tray thereby being tiltable about a second horizontal axis between said waiting position and said exposure position.

3. The improvement according to claim 2, wherein said first horizontal axis is arranged parallel to said second horizontal axis.

4. The improvement according to claim 2, wherein said means for transferring said film cassette tray from said waiting position to said exposure position is pivotly connected to said means for moving said X-ray tube from said first to said second position.

5. The improvement according to claim 2, wherein said mounting device comprises a mounting arm connected to said lower end of said column and extending in a horizontal direction.

6. The improvement according to claim 5, wherein said first and second horizontal axes are arranged perpendicularly to the longitudinal axis of said horizontal mounting arm.

7. The improvement according to claim 2, wherein said mounting device comprises first locking means for locking said X-ray tube in said first position and second locking means for locking said X-ray tube in said second position.

8. The improvement according to claim 2, wherein said X-ray tube is arranged on said first side and said film cassette tray is arranged on said second side with respect to the longitudinal axis of said support column.

9. The improvement according to claim 2, wherein said first horizontal axis is arranged on said first side and said second horizontal axis is arranged on said second side of the longitudinal axis of said support column.

10. The improvement according to claim 2, wherein said first and said second horizontal axes are located below said lower end of said support column.

11. The improvement according to claim 2, wherein said mounting device contains an extension piece extending vertically such that in said second position said X-ray tube and said film cassette tray are located below said lower end of said support column.

12. The improvement according to claim 2, wherein in said waiting position and film cassette tray extends upwardly, and wherein in said first position said X-ray tube is adapted to emit said X-ray beam downwardly.

13. The improvement according to claim 1, wherein said positioning and transferring means are lever means.

14. The improvement according to claim 1, wherein said means for moving said X-ray tube between said first and second position are lever means.

15. The improvement according to claim 2, wherein said X-ray tube is attached to at least one first lever, one end portion of which is tiltable about said first horizontal axis, and wherein said cassette tray is attached to at least one second lever, one end portion of which is tiltable about said second horizontal axis.

16. The improvement according to claim 13, wherein said positioning and transferring means comprise two lever systems which are arranged parallel to each other.

17. The improvement according to claim 14, wherein said moving means comprise two lever systems which are arranged parallel to each other.

18. The improvement according to claim 16, wherein said cassette tray is connected to two curved levers which are arranged parallel to each other, and wherein a control box is located between said two curved levers.

19. The improvement according to claim 15, wherein said moving means comprises a first knee joint which is connected with its one end portion to said first lever and with its other end portion to a common pivotal axis which is provided in said mounting device; and wherein said transferring means comprises a second knee joint which is connected with its one end portion to said second lever and with its other end portion to said common pivotal axis in said mounting device.

20. The improvement according to claim 13 or 14, wherein a plurality of levers is united in a plate, and wherein a common pivotal axis is provided in said mounting device for pivoting said plate thereabout.

21. The improvement according to claim 20, wherein said plate is provided with three connection points, whereby one of said points is provided for a first knee joint, a second one for a second knee joint and a third one for a spring.

22. The improvement according to claim 1, wherein said transferring means comprises a spring for smoothing the transition from said first to said second position.

23. The improvement according to claim 22, wherein said spring is a gas compression spring.

* * * * *